(12) United States Patent
Nelson et al.

(10) Patent No.: US 7,185,983 B2
(45) Date of Patent: Mar. 6, 2007

(54) SYSTEM AND METHOD FOR DISPLAYING INFORMATION ON ATHLETIC EYEWEAR

(75) Inventors: Andrew Nelson, 6515 James Rd., Bettendorf, IA (US) 52722; Umar W. Ansari, Arlington, VA (US)

(73) Assignee: Andrew Nelson, Bettendorf, IA (US)

( * ) Notice: Subject to any disclaimer, the term of this patent is extended or adjusted under 35 U.S.C. 154(b) by 0 days.

(21) Appl. No.: 10/822,909

(22) Filed: Apr. 13, 2004

(65) Prior Publication Data

US 2005/0225868 A1    Oct. 13, 2005

(51) Int. Cl.
G02C 7/02    (2006.01)
A63B 71/10    (2006.01)

(52) U.S. Cl. ............................ 351/159; 351/177; 2/425
(58) Field of Classification Search ................ 351/177, 351/159; 2/425, 426; D16/101, 300, 309, D16/330
See application file for complete search history.

(56) References Cited

U.S. PATENT DOCUMENTS

| | | | |
|---|---|---|---|
| 4,181,405 A * | 1/1980 | Cohen ........................... 349/11 |
| 4,526,473 A | 7/1985 | Zahn, III |
| 4,757,714 A | 7/1988 | Purdy et al. |
| 4,776,045 A | 10/1988 | Mysliwiec et al. |
| 4,796,987 A | 1/1989 | Linden |
| 5,258,785 A | 11/1993 | Dawkins, Jr. et al. |
| 5,266,977 A | 11/1993 | Linden |
| D352,513 S * | 11/1994 | Schwartz .................... D16/309 |
| 5,446,506 A | 8/1995 | Dawklins, Jr. |
| 5,585,871 A | 12/1996 | Linden |
| 5,594,573 A * | 1/1997 | August ......................... 349/13 |
| 6,033,228 A * | 3/2000 | Ladin .......................... 434/254 |
| 6,204,974 B1 * | 3/2001 | Spitzer ........................ 359/630 |
| 6,705,725 B2 * | 3/2004 | Gotoh et al. ................. 351/159 |
| 6,870,466 B2 * | 3/2005 | Rust et al. ............... 340/323 R |
| 6,947,014 B2 * | 9/2005 | Wooten .......................... 345/8 |
| 2003/0030597 A1 | 2/2003 | Geist |
| 2003/0189484 A1 | 10/2003 | Rust et al. |
| 2004/0054031 A1 * | 3/2004 | Jacobson ..................... 523/160 |
| 2004/0125348 A1 * | 7/2004 | Carkner ....................... 353/119 |

FOREIGN PATENT DOCUMENTS

WO    WO 94/09398    *    4/1994

OTHER PUBLICATIONS

"Wireless for the Disabled", *Technology Review*, www.technologyreview.com,(Dec. 2003/Jan. 2004),65-66.

* cited by examiner

*Primary Examiner*—Jordan M. Schwartz
(74) *Attorney, Agent, or Firm*—Schwegman, Lundberg, Woessner & Kluth

(57) ABSTRACT

A system and method of displaying performance information on athletic eyewear. A display is formed and attached to or embedded in one or more lens of an article of athletic eyewear. The display is then activated to display the performance information.

15 Claims, 8 Drawing Sheets

SYSTEM AND METHOD FOR DISPLAYING INFORMATION ON ATHLETIC EYEWEAR

BACKGROUND OF THE INVENTION

1. Field of the Invention

The present invention is related to display technologies, and more particularly to a system and method for displaying information on athletic eyewear.

2. Background Information

Athletes aiming to increase their performance in their sports often use elapsed time both as a measure of performance and as a motivator for increased effort. Oftentimes, this means tracking time with a wrist-mounted watch or stopwatch, or relying on clocks mounted in the exercise facility. Other performance indicators (such as distance traveled or pulse rate) also are typically displayed on a wrist-mounted display. The effort of looking at a watch, clock or other such display creates a break in the workout, and extra energy must be spent to come back to speed and focus.

Systems have been proposed for displaying information such as elapsed time on athletic eyewear. Attempts to date have required bulky add-on units which have a tendency to come apart under the rigors of performance training.

What is needed is a system and method of displaying performance information on athletic eyewear that addresses these and other concerns as described below.

DETAILED DESCRIPTION OF THE INVENTION

In the following detailed description of the preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Figure 1:
FIGS. 1 and 2 illustrate one example of athletic eyewear according to the present invention.
Figure 2:
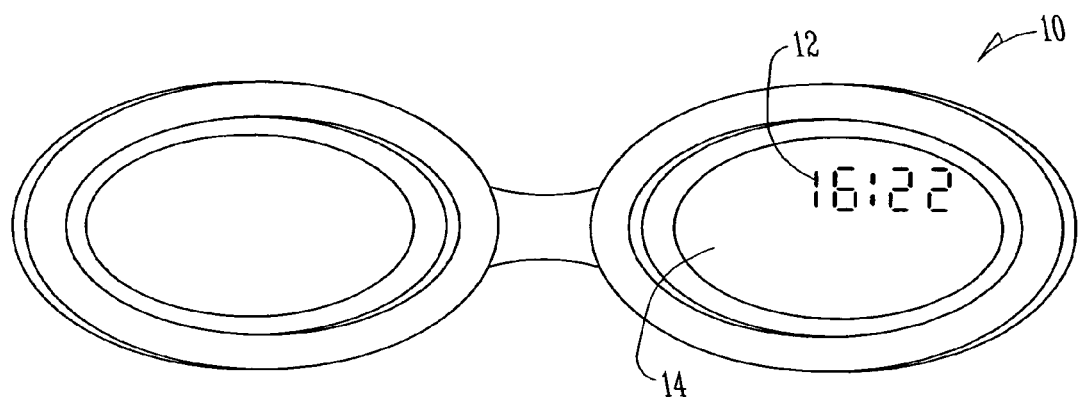

An example of athletic eyewear capable of displaying performance information is shown in FIGS. 1 and 2. FIGS. 1 and 2 illustrate a pair of swim goggles 10. Swim goggles 10 include a band 16, a display 12 and one or more lenses 14. In contrast to previous approaches in which the display is an add-on to existing eyewear, in the example shown in FIGS. 1 and 2, display 12 is an integral part of one or more of the lenses 14 of swim goggles 10. This provides advantages in terms of durability, weight and ease of use.

Figure 3:
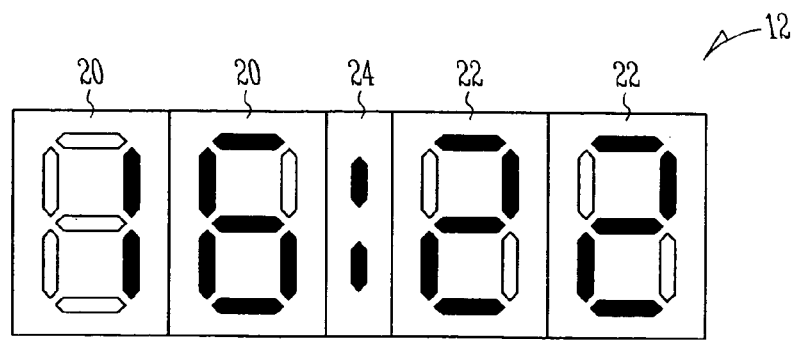
FIGS. 3 and 4 illustrate displays that can be used in the athletic eyewear of FIGS. 1 and 2.
Figure 4:
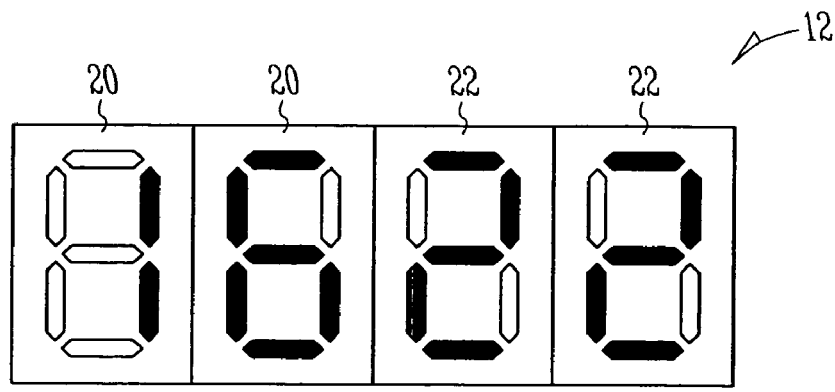

A more detailed illustration of one embodiment of display 12 is shown in FIG. 3. In the example shown in FIGS. 1–3, display 12 includes two seven-segment sections 20 for displaying minutes, two seven-segment sections 22 for displaying seconds and a two-segment section 24 for displaying a symbol such as a colon. In another embodiment, only sections 20 and 22 are used (i.e., there is no symbol separating minutes from second). Such an embodiment is shown in FIG. 4.

Figure 5:
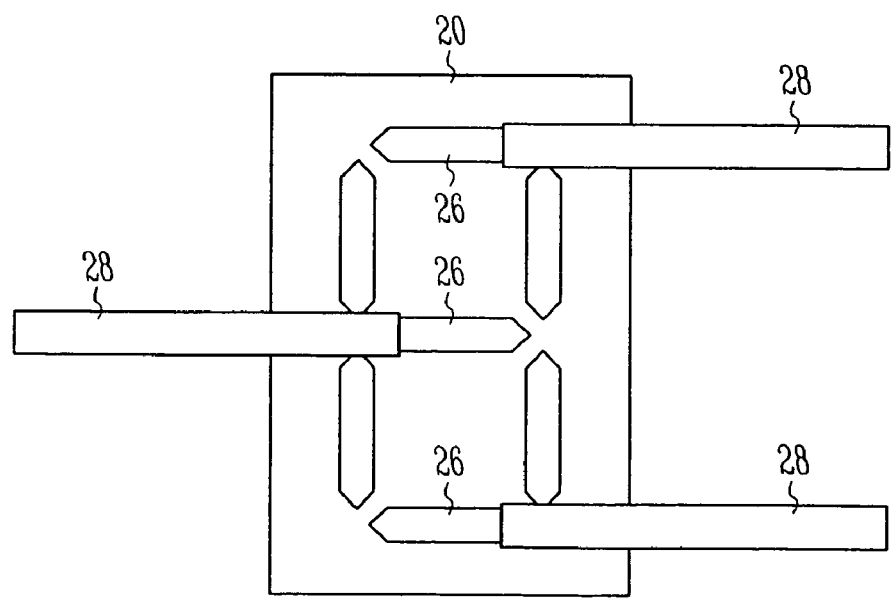
FIGS. 5–7 illustrate embodiments of display sections that can be used in the displays of FIGS. 3 and 4.

As noted above, display 12 is an integral part of lens 14. In one embodiment, each segment 26 in sections 20 and 22 is formed from light pipes 28. As shown in FIG. 5, a separate light pipe 28 carries light to each of the segments 26. (In the example shown in FIG. 5 only three light pipes 28 are shown. This was done to reduce complexity in the drawings. There would be seven light pipes 28 for each section 20 or 22, two for each section 24.)

Figure 6:
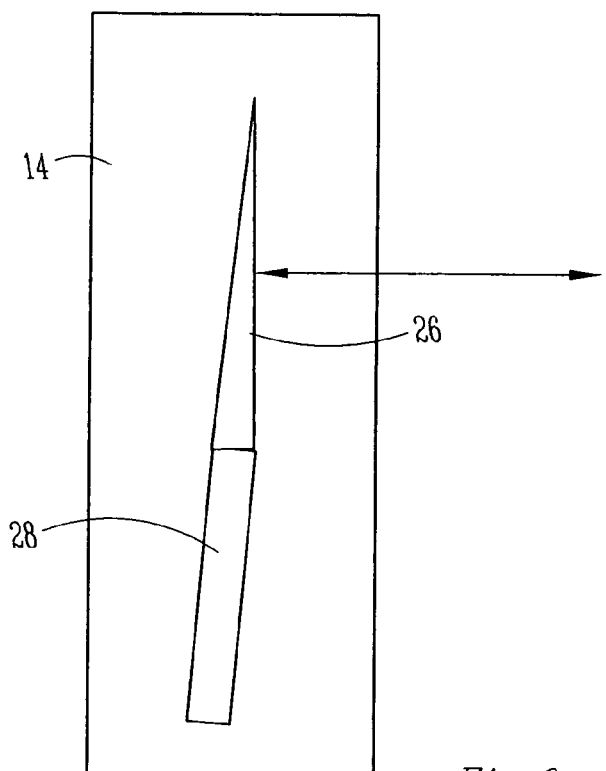
Figure 7:
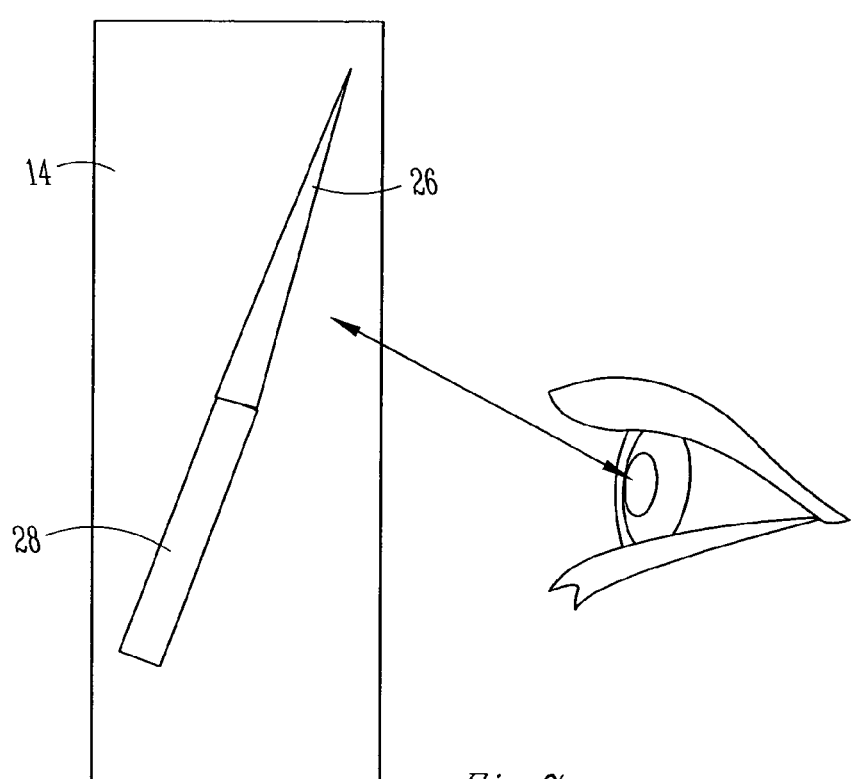

In one such approach, segment 26 is formed by cutting a translucent line such as fishing line at an angle to form an ellipse and orienting the ellipse for viewing by the user. In one such embodiment, as is shown in FIG. 6, the surface of the ellipse is oriented parallel to the surface of lens 14. In another such embodiment, as is shown in FIG. 7, the surface of the ellipse is oriented orthogonally to the angle of viewing of the wearer of the goggles 10 such that the user sees the greatest surface area of the ellipse.

In one embodiment, lens 14 is formed from resin. Each light pipe 28 is embedded in the resin as part of the manufacture of lens 14. In one such embodiment, a lens 14 is formed by pouring resin into a mold and suspending display 12 in the resin prior to hardening. In another such embodiment, a lens 14 is formed by pouring resin into a mold and suspending a plurality of light pipes in the resin in the desired configuration prior to hardening.

In one embodiment, light pipes from each of the segments 20, 22 and 24 are bundled and embedded in band 16. It can be advantageous to treat the outside surface of light pipes 28 to increase their reflectivity (e.g., to minimize transmission losses). The lens is then mounted in the athletic eyewear.

Figure 8:
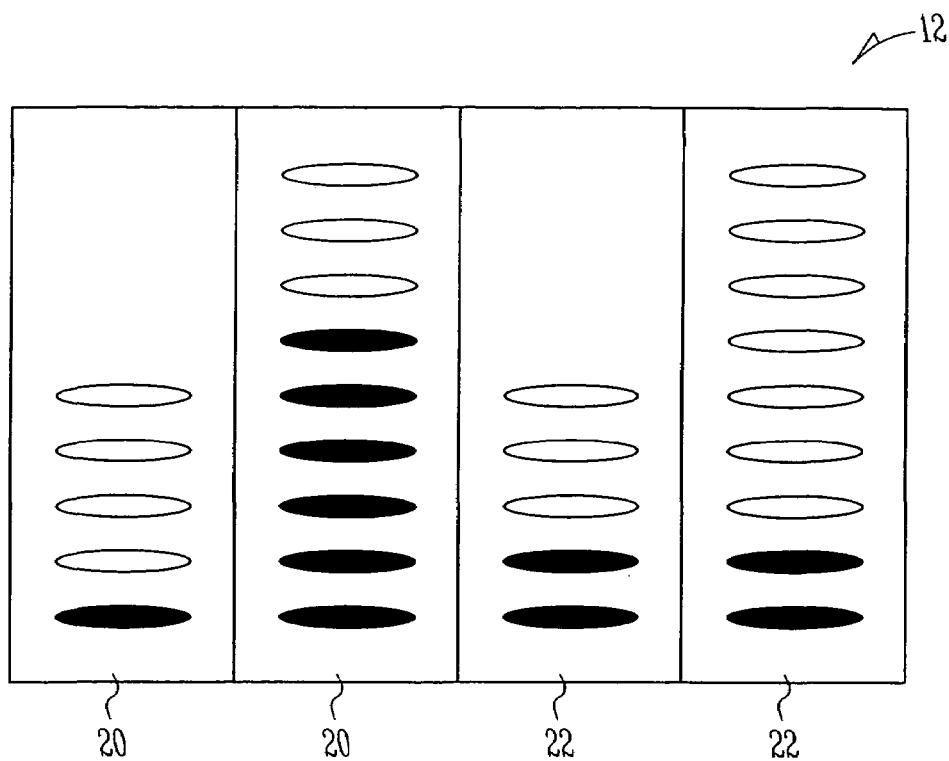
FIG. 8 illustrates a display that can be used in the athletic eyewear of FIGS. 1 and 2.

FIG. 8 illustrates a graphical representation of the time displayed in FIGS. 2, 3 and 4. Once again, each of the segments 30 is formed from a light pipe 28 cut at an angle to form an ellipse. As before, lens 14 is formed from resin and each light pipe 28 is embedded in the resin as part of the manufacture of lens 14.

Figure 9:
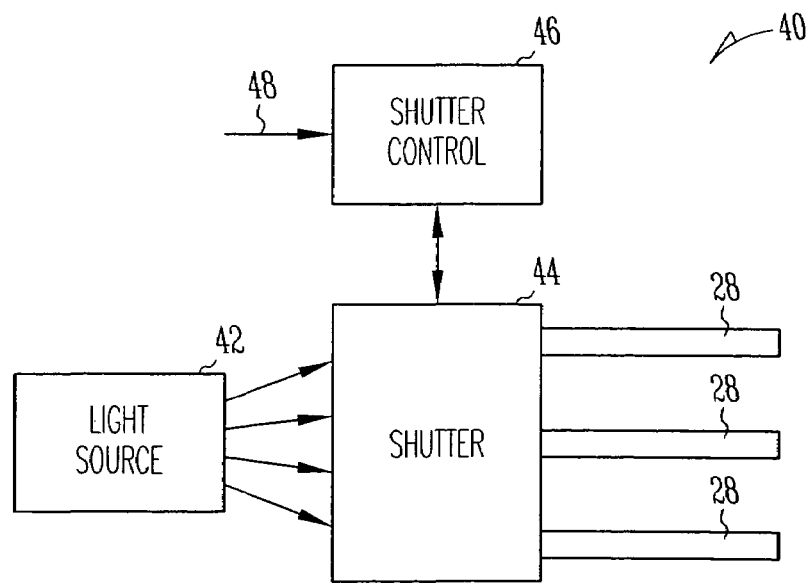
FIG. 9 illustrates a display controller according to the present invention.

A display controller 40 capable of driving display 12 is shown in FIG. 9. In the embodiment shown, display controller 40 includes a light source 42, a shutter mechanism 44 and a shutter control 46. In one embodiment, light source 42 includes one or more LEDs or other such light source positioned to direct light toward shutter mechanism 44.

Shutter mechanism 44 can be any mechanism that shuts off light to individual light pipes 28.

In one embodiment, shutter mechanism 44 is formed by coating an end of each light pipe 28 with a material that turns opaque to visible light when charged. A charge sensitive material can be used to create the shutter. Examples of charge sensitive materials include suspended particle devices (SPD), polymer dispersed liquid crystals (PDLC) and electrochromatic films (ECF).

Shutter control 46 provides the signals which turn on and off the light to each of the light pipes 28. In one embodiment, shutter control 46 is a microcontroller such as a PIC microcontroller available from Microchip Technology Inc. of Itasca, Ill. In one such embodiment, the PIC microcontroller is packaged with EEPROM as a Basic Stamp. Such embodiments are available from Parallax, Inc. of Rocklin, Calif.

Figure 10A:
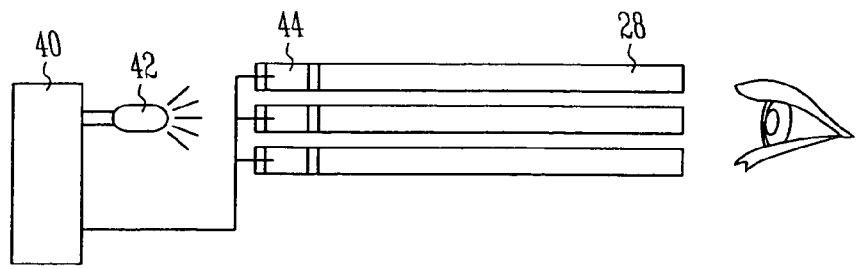
FIGS. 10a–10c illustrate different embodiments of shutter mechanisms which can be used in the system shown in FIG. 9.
Figure 10B:
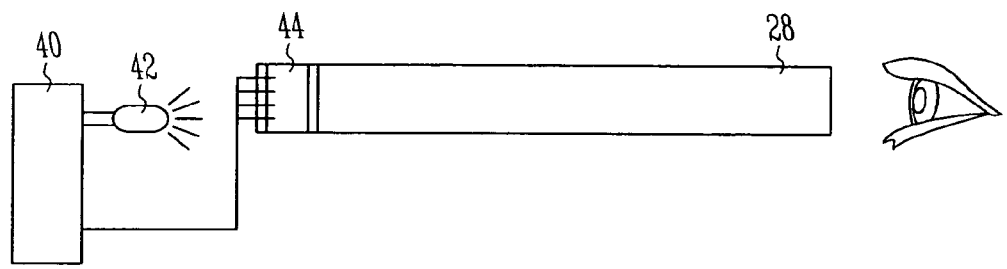
Figure 10C:
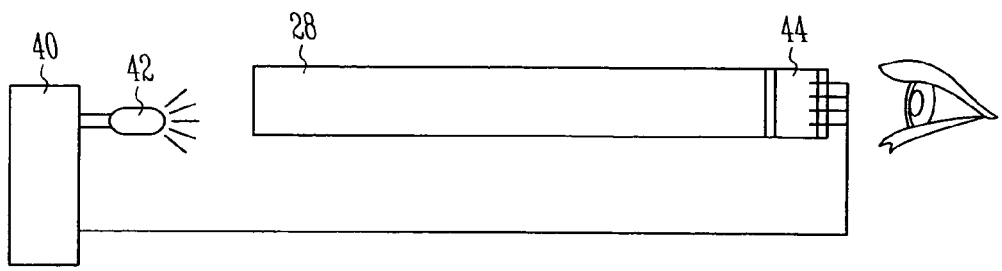

Three embodiments of shutter mechanism 44 are shown in FIGS. 10*a*–*c*. In the embodiment shown in FIG. 10*a*, light pipes 28 are backlit with a single LED. A SPD or PDLC coating is applied to the light pipe 28 at the end furthest from the user's eye. There exists a coating individually on each light pipe and each coating is connected to the display driver individually. The driver charges the SPD or PDLC coating to illuminate a segment of the display.

In the embodiment shown in FIG. 10*b*, each light pipe 28 is illuminated by one or more LEDs. The end of the light pipe furthest from the eye is coated with an array of SPD or PDLC nodes. The driver is connect to the array of nodes and charges each node individually to illuminate a segment of the display.

In the embodiment shown in FIG. 10*c*, each light pipe 28 is illuminated by one or more LEDs. The end of the light pipe closest to the eye is coated with an array of SPD or PDLC nodes. The driver is connect to the array of nodes and charges each node individually to illuminate a segment of the display. Such an approach reduces the effects of image pipe quality on image resolution, allowing the use of lower quality light pipes. In one such embodiment, the SPD and PDLC nodes are connected by wires to the display driver. The wires run parallel to each light pipe 28.

ECF could be used in a similar way.

In one embodiment, in addition to controlling shutter mechanism 44, shutter control 46 is programmed to provide the stop watch function as well. In one such embodiment, a button connected to interface 48 tells shutter control 46 when to start and stop counting seconds. A second button connected to interface 48 tells shutter control 46 when to clear its counter. Other approaches can be used as well.

In one embodiment, device 40 is mounted adjacent to display 12 on goggles 10. Such an approach reduces the losses in light transmitted through light pipes 48. In one such embodiment, device 40 is formed into the body of goggles 10 in order to reduce drag.

Figure 11:
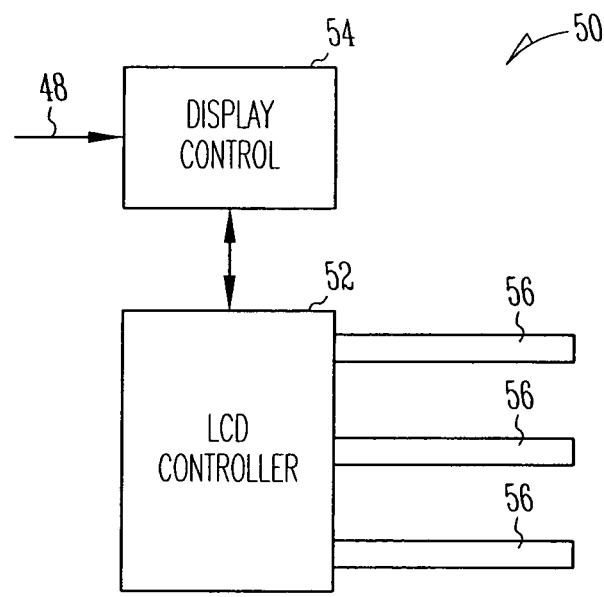
FIGS. 11 and 12 illustrate alternate display controllers according to the present invention.

Display 12 as shown in FIG. 3 can be implemented in other ways as well. For instance, display 12 can be implemented as an off-the-shelf transparent liquid crystal display (LCD). In one such embodiment, a lens 14 is formed by pouring resin into a mold and suspending the LCD in the resin prior to hardening. In that case, light pipes 28 are replaced by electrical wires 56, and light source 42 and shutter mechanism 44 of FIG. 8 are replaced by an LCD controller 52 in device 50. An example embodiment is shown in FIG. 11. SPD and ECF devices could be embedded in display 12 in a similar way.

A microcontroller similar to that used for shutter control 46 can be used for display control 54. Operation of display control 54 is as discussed above.

In one embodiment, the LCD display and its attached electrical wires 56 are embedded in the resin as part of the manufacture of lens 14. In another embodiment, the LCD display is packaged in a translucent tape for application to the outside of a lens of swim goggles 10.

Once again, in one embodiment, display controller 50 is mounted adjacent to display 12 on goggles 10. Such an approach reduces the losses in light transmitted through light pipes 48. In one such embodiment, display controller 40 is formed into the body of goggles 10 in order to reduce drag. Ambient light should be sufficient to illuminate the LCD display in most exercise environments. Where ambient light is not sufficient a backlight can be provided to illuminate display 12.

Figure 12:
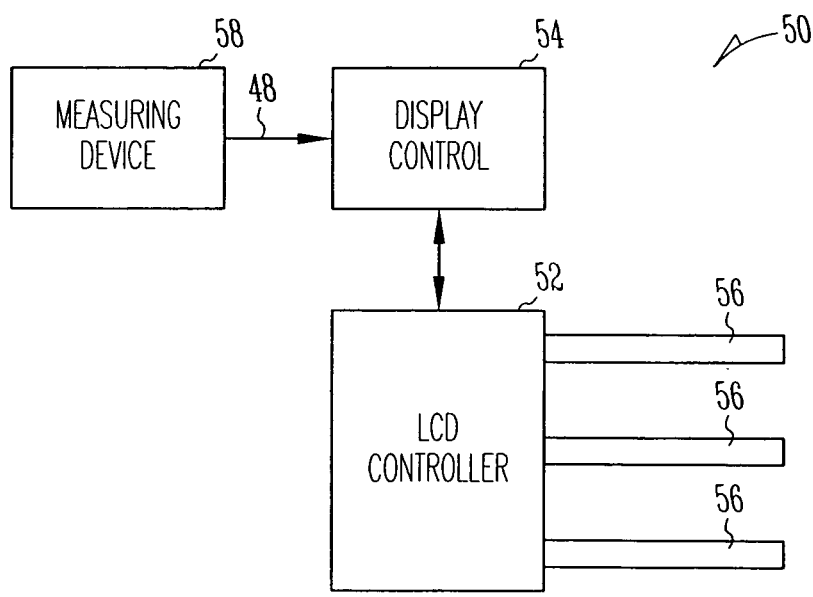

Interface 48 can be connected to more than just one or more buttons. For instance, as is shown in FIG. 12, in one embodiment a measuring device 58 measures information such as heart rate and transmits the measured heart rate to display control 54 (or shutter control 46) for display on display 12. In another embodiment, measuring device 58 includes an accelerometer used to detect a flip turn while swimming. Display 12 can then be used to display a lap count. Other information could be displayed as well. One could display music information received from, for instance, an Apple IPOD. A wireless connection to interface 48 could be used to lad stock quotes, odometer readings, etc. to display control 54 and, from there, to display 12. A wireless protocol such as Bluetooth can be used advantageously is such situations.

Figure 13:
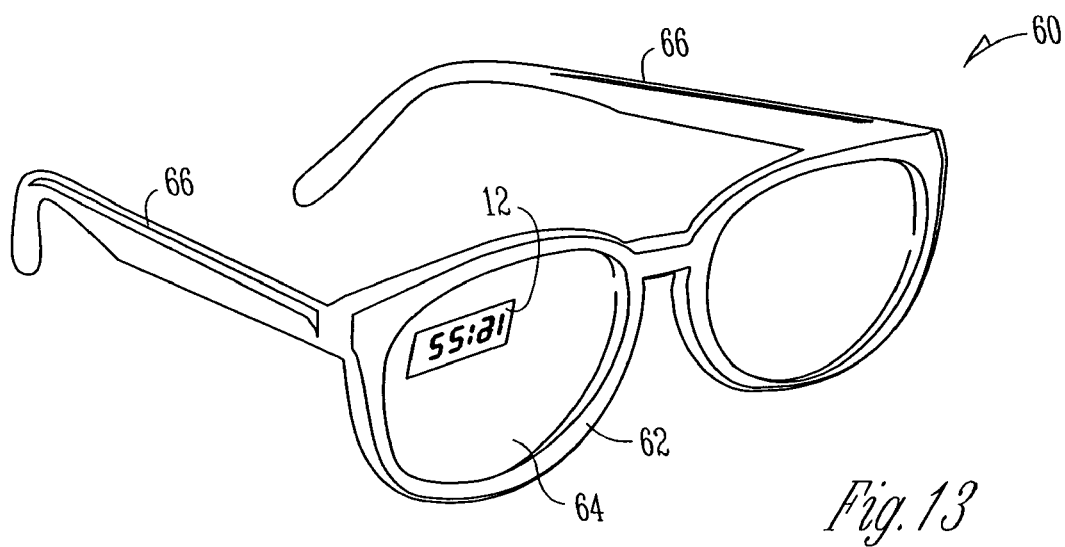
FIG. 13 illustrates another example of athletic eyewear according to the present invention.

Another example of athletic eyewear capable of displaying performance information is shown in FIG. 13. FIG. 13 illustrates a pair of glasses 60 having a frame 62, one or more lenses 64 and arm pieces 66 that drape over the user's ears. In the embodiment shown in FIG. 13, a display 12 is embedded in one or more of the lenses 64 in the manner discussed above. In one such embodiment, the bundle of light pipes 48 is configures so that it can be attached to one of the arm pieces 66. In another embodiment, wires 56 are embedded within one of the arm pieces 66 during the frame manufacturing process.

As in the example for goggle 10 above, devices 40 and 50 can be used to drive display 12. In one embodiment, devices 40 and 50 are manufactured as an integral part of frame 62.

There are many advantages to the approaches for displaying performance information discussed above. The above-described goggles are lighter in weight and more durable than previous attempts at displaying such information. In addition, since both displays are embedded in the lens, or securely attached to the outside of the lens, the user should experience less vibration and a larger field of view. Finally, the light pipe solution provides a brighter, more ergonomic solution at a reasonable cost.

Portions of the above description have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, terms such as "processing" or "computing" or "calculating" or "determining" or "displaying" or the like, refer to the action and processes of a computer system, or similar computing device, that manipulates and transforms data represented as physical (e.g., electronic) quantities within the computer system's registers and memories into other data similarly represented as physical quantities within the computer system memories or registers or other such information storage, transmission or display devices.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. A method of displaying performance information on athletic eyewear, comprising:
    forming a lens, wherein forming includes embedding a plurality of light up segments and a plurality of light pipes in the lens in order to form a segment display in the lens, wherein each light pipe is associated with a separate segment to be lit;
    mounting the lens in the athletic eyewear; and
    activating the display from a source outside the lens.

2. The method according to claim 1, wherein forming includes pouring resin in a mold and wherein embedding includes suspending the plurality of light pipes in the resin prior to hardening.

3. The method according to claim 1, wherein activating the display includes receiving information from a measuring device and driving the display as a function of the information received from the measuring device.

4. A method of displaying performance information on athletic eyewear, comprising:
    forming a lens, wherein forming includes pouring resin in a mold and suspending a plurality of light up segments and a plurality of light pipes in the resin prior to hardening, wherein each light pipe is associated with a separate segment to be lit;
    mounting the lens in the athletic eyewear; and
    activating the display from a source outside the lens;
    wherein the display is a segment display and wherein activating the display includes directing light into the light pipe associated with each segment to be lit.

5. The method according to claim 4, wherein each light pipe is attached to a shutter and wherein directing the light into a light pipe includes opening the shutter attached to the light pipe.

6. The method according to claim 4, wherein activating the display includes receiving information from a measuring device, determining which segments to light as a function of the information received from the measuring device and directing light into a light pipe associated with each segment to be lit.

7. The method according to claim 6, wherein each light pipe is attached to a shutter and wherein directing the light into a light pipe includes opening the shutter attached to the light pipe.

8. Athletic eyewear capable of displaying information, comprising:
    a frame;
    a lens, wherein the lens includes a plurality of light up segments and a plurality of light pipes embedded within the lens, wherein the plurality of light pipes and the plurality of light up segments are configured to form a segment display, wherein each light pipe is associated with a separate segment to be lit and wherein the lens is mounted in the frame such that the display is viewable by a user wearing the eyewear; and
    a display controller, wherein the display controller drives the display as a function of the information to be displayed.

9. The athletic eyewear of claim 8, wherein each light pipe includes a shutter formed by coating an end of the light pipe with a material which changes opacity under electrical charge.

10. Athletic eyewear capable of displaying information, comprising:
    a frame;
    a lens, wherein the lens includes a display embedded within the lens, wherein the lens is mounted in the frame such that the display is viewable by a user wearing the eyewear; and
    a display controller, wherein the display controller drives the display as a fraction of the information to be displayed;
    wherein the display comprises a plurality of light up segments and a plurality of light pipes, wherein each light pipe is associated with a separate segment to be lit and wherein an end of each light pipe is attached to a shutter.

11. The athletic eyewear of claim 10, wherein the shutter is formed by coating an end of the light pipe with a material which changes opacity under electrical charge.

12. A method of displaying performance information on athletic eyewear, comprising:
    forming a segment display from a plurality of light up segments and a plurality of light pipes wherein each light pipe is associated with a separate segment to be lit;
    attaching the display to one or more lens of an article of athletic eyewear; and
    activating the display to display the performance information, wherein activating the display includes directing light into the light pipe associated with each segment to be lit.

13. The method according to claim 12, wherein activating the display includes receiving information from a measuring device and driving the display with a controller as a function of the information received from the measuring device.

14. The method according to claim 12, wherein attaching includes pouring resin in a mold and suspending the display in the resin prior to hardening.

15. The method according to claim 12, wherein each light pipe is attached to a shutter and wherein directing light into a light pipe includes opening the shutter attached to the light pipe.

* * * * *